United States Patent [19]

Ohashi et al.

[11] 4,297,198

[45] Oct. 27, 1981

[54] CONCENTRATING ELECTROPHORESIS APPARATUS

[76] Inventors: Mochihiko Ohashi, 2-33-16-507, Tokiwadai, Itabashi-ku, Tokyo; Tosifusa Toda, 2-6-4, Shinpo-cho, Higashikurume-shi, Tokyo, both of Japan

[21] Appl. No.: 190,869

[22] PCT Filed: May 29, 1979

[86] PCT No.: PCT/JP79/00137

§ 371 Date: Jan. 8, 1980

§ 102(e) Date: Jan. 8, 1980

[87] PCT Pub. No.: WO79/01141

PCT Pub. Date: Dec. 27, 1979

[30] Foreign Application Priority Data

May 29, 1978 [JP] Japan ................................ 53-64307

[51] Int. Cl.³ .................... G01N 27/26; C25B 7/00
[52] U.S. Cl. .................... 204/299 R; 204/180 G; 204/180 S; 424/12
[58] Field of Search .......... 204/180 G, 180 S, 299 R; 23/230 B; 424/12

[56] References Cited

U.S. PATENT DOCUMENTS

| | | | |
|---|---|---|---|
| 3,303,120 | 2/1967 | Hrdina | 204/300 R |
| 3,421,998 | 1/1969 | Yallen | 204/299 R |
| 3,494,846 | 2/1970 | Arquembourg | 204/180 G |
| 3,720,593 | 3/1973 | Juhos | 204/180 G |
| 3,755,121 | 8/1973 | Schlutz | 204/180 G |
| 3,856,656 | 12/1974 | Brink | 204/180 G X |
| 3,873,433 | 3/1975 | Seidel et al. | 204/180 G |
| 4,059,501 | 11/1977 | Strickler | 204/180 G X |
| 4,142,960 | 3/1979 | Hahn et al. | 204/299 R |

Primary Examiner—Arthur C. Prescott
Attorney, Agent, or Firm—Wenderoth, Lind & Ponack

[57] ABSTRACT

In a so-called membrane electrophoresis apparatus used for separating a liquid sample containing components having biological activity such as various proteins into the components, there is provided an apparatus for simplifying the operation of applying the liquid sample on a supporting membrane and, moreover, for separating with good accuracy the above mentioned components. A supporting medium (3) for separation comprising a water-retentive membrane material and electrically connected to one electrode (5a) of a direct-current electric power source is wetted by a buffer solution (A) containing leading ions. A supporting medium (7c) and a supporting medium (9) similarly comprising water-retentive materials are respectively wetted by a buffer solution (C) containing terminating ions and a buffer solution containing leading ions and having a pH which is different from that for the above mentioned supporting medium for separation. In the state of use, after the liquid sample is applied in a linear form on the middle of the supporting medium (9), the supporting medium (9) is caused to contact at its two ends the supporting medium (3) and the supporting medium (7c) (FIG. 3), and the entire assembly assumes an electrically conductive state. The sample progressively migrates toward the electrode (5a), but because of the sharp interfaces formed by the leading ions and the terminating ions during this operation, the sample is once concentrated on the supporting medium (9) and, as it migrates toward the supporting medium (3), is separated with good accuracy into the respective components.

11 Claims, 3 Drawing Figures

CONCENTRATING ELECTROPHORESIS APPARATUS

DESCRIPTION

1. Technical Field

This invention relates to an electrophoresis apparatus for carrying out separation of multicomponent samples by means of water-retentive supporting media in sheet form or membrane form and more particularly relates to an electrophoresis apparatus characterized in that, by being provided with means for once carrying out electrophoretic concentration of the components on the supporting medium, it is made capable of separating with high accuracy the multicomponent sample in the succeeding phoretic separation step.

2. Background Art

Electrophoresis wherein a water-retentive, sheet-form or membrane-form materials such as filter paper or cellulose acetate membrane (hereinafter referred to collectively as membrane-form material or simply as membrane) is used for separating charged particles of biological components having biological activity and other components (hereinafter referred to as generically as membrane electrophoresis) is being widely used because of its simplicity. This membrane electrophoresis, simply stated, is a process utilizing the phenomenon by which, when a sample solution such as blood serum is applied on a membrane wetted with a buffer solution, and a dirent-current electric field is applied, the sample components comprising individual proteins, etc., separate on the membrane in accordance with the differences in mobilities governed principally by their quantities of charge depending on the pH of the buffer solution, and these separated sample components are, for example, dyed or otherwise treated and subjected to identification and determination. In comparison with the block or gel electrophoresis, this membrane electrophoresis has the advantage in that it is extremely simple and convenient because there is no necessity of the experimenter to prepare the supporting medium, and a commercially available membrane-form supporting medium of uniform quality can be used as it is. Moreover, since excellent materials for supporting media such as cellulose acetate membrane are abundantly sold on the market, it is widely used for routine tests. However, there are problems in that the above mentioned application of the sample solution onto the membrane-form supporting medium is technically difficult and requires skill and in that the propriety thereof exerts a great influence on the analysis result. That is, in the analysis, it is necessary to apply the sample by means of micropipette or the like on the support medium in the form of a thin straight line perpendicular to the straight line joining the electrodes of the direct-current power source connected to the supporting medium, but the uniform application of such a thin straight line is not easy. Furthermore, when the sample is not applied well in the thin-line form, the separation of the components becomes very poor. Particularly in the case where sample (protein) concentration is low as in an extract from liver or some other tissue, it is necessary in order to increase the accuracy of analysis to apply the sample in a great quantity (for example, of the order of 10 $\mu$l relative to 0.5 $\mu$l of blood serum or the like), but in such a case, even if the application of the sample is carried out ideally, there will be the difficulty that the separation of the components becomes very poor.

DISCLOSURE OF INVENTION

It is an object of this invention to provide a novel membrane electrophoresis apparatus which makes it possible to overcome the difficulty of applying the sample liquid, which is a problem accompanying the membrane electrophoresis as described above, while retaining the advantages thereof. As a result of research conducted by the present inventors, it has been found that this object can be achieved by an electrophoresis apparatus which is provided with a mechanism for making it possible to concentrate the same liquid on the supporting medium at an initial stage of the electrophoresis operation. This invention is characterized in that this concentration is carried out by means of an electrophoretic concentrating apparatus comprising: supply means for a buffer solution containing terminating ions connected to one electrode of a direct-current (dc) or alternating-current (ac)-superposed dc power source (hereinafter referred to simply as "dc power source"); a supporting medium for concentration comprising a water-retentive membrane material wetted with a buffer solution containing leading ions; and a movable mechanism for causing this supporting medium for concentration to contact at its one end the aforementioned supply means and impart electrical connection between the supporting medium for concentration and the supply means. This invention relates to an electrophoresis apparatus capable of concentration and separation by the incorporation thereinto of the above described electrophoretic concentrating apparatus and the further provision therein of a supporting medium for separation for the purpose of imparting thereto the capability of separating electrophoresis apparatus of the invention is characterized in that it comprises: supply means for a buffer solution (solution C) containing terminating ions and electrically connected to one electrode of a dc power source; a supporting medium for separation comprising a water-retentive membrane material electrically connected to the other electrode of the dc power source and moreover, wetted by a buffer solution (solution A) containing leading ions; a supporting medium for concentration comprising a water-retentive membrane material containing leading ions and, moreover, wetted by a buffer solution (solution B) of a pH different from that of the above-mentioned buffer solution wetting the supporting medium for separation; and a movable mechanism for causing the supporting medium for concentration to contact at its one end the aforementioned supply means and impart electrical connection through the supply means, supporting medium for concentration, and supporting medium for separation.

On the point of using a discontinuous buffer solution system, thereby concentrating the sample components on a sharp ion interface formed between leading ions and terminating or trailing ions, and the separating them, the operation of the apparatus of this invention in some respects is similar to the disk electrophoresis (Ornstein, L., Davis, B. J.: Preprint by Distillation, Products Industries, 1962; Ornstein, L: Annuls of the New York Academy of Sciences., 121 321 (1964); etc.). Here, the terms "leading ions" and "terminating ions" may be defined as ions having electric charges of the same sign as the sample components to be separated under the given electrophoresis conditions and, moreover, respectively having "greater" and "less" mobilities than any of the sample components. However, whereas, in the disk electrophoresis, the formation of an ion interface as mentioned above is made possible by the use of a polyacrylamide gel or the like of low permeation or convection of water, in this invention, the formation of an ion interface is made possible by an organization such that, on a membrane material of high permeation or convection of water, the contacting of two buffer solution systems and the electrical conduction can be simultaneously started, whereby this invention is completely different from the viewpoint of an organization. Also, accordingly, the difficulty of preparing the supporting medium (gel column) which is encountered in the disk electrophoresis is eliminated, and analysis with good reproducibility is made possible. This is the greatest significance of this invention.

BEST MODE FOR CARRYING OUT THE INVENTION

Figure 1:
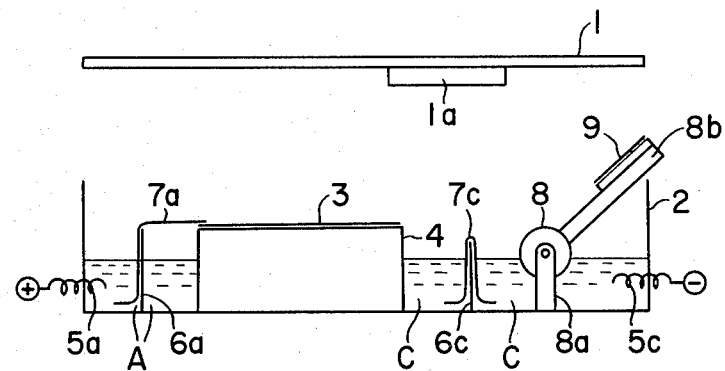
FIG. 1 is a conceptual general arrangement view as viewed from the side for the purpose of illustrating the organization and operation of one example of practice of the concentrating electrophoresis apparatus of the invention.

In FIG. 1, the membrane concentrating electrophoresis apparatus is placed in a vessel 2 of relatively great side width having a cover 1. At substantially the middle part of the vessel 2, a cooling water circulation chamber 4 in the interior of which cooling water is circulated for the purpose of removing the Joule heat of electrophoresis from a supporting medium 3 for separation is disposed, and thereabove, a porous cellulose acetate membrane 3 (manufactured by Fuji Shashin Film Co., Separax-EF, thickness 140 $\mu$m, specific gravity approximately 0.3) cut to 60×85 mm. as the supporting medium for separation is placed over a glass plate (70×90×1 mm., not shown). The cooling water circulation chamber 4 divides the vessel 2 into left and right parts and forms two chambers, namely, an anode chamber A and a cathode chamber C. In the chamber A is placed 22 ml. of a buffer solution (solution A) prepared by dissolving 44.8 grams (g.) of Tris (that is, trishydroxymethylaminomethane) in distilled water, adjusting the pH to 8.9 with approximately 59 ml. of 1-normal hydrochloric acid, and then further increasing the volume to 1 liter with distilled water, and in the chamber C is placed 35 ml. of a buffer solution (solution C) prepared by dissolving 22.88 g. of glycine in distilled water, adjusting the pH to 8.3 with approximately 50 ml. of Tris of 1 mol concentration, and then further increasing the volume to 1 liter by adding distilled water. Here, $Cl^-$ ions become leading ions, while glycine$^-$ ions become terminating ions. Furthermore, in the chamber A and the chamber C, respectively, a dc anode 5a and a dc cathode 5c ordinarily made of platinum and a filter-paper support plate 6a for supplying the solution A and a filter-paper support plate 6c for supplying the solution C are inserted. The support plate 6a supports a bridge 7a of filter paper (70×40×1 mm.) passed thereover thereby to cause the solution A and the supporting medium 3 for separation to contact and to supply the solution A to the supporting medium 3 by the capillary phenomenon of the filter paper and, further, affords electrical connection between the anode 5a and the supporting medium 3 for separation. A filter-paper bridge 7c is similarly passed over the support plate 6c, and its top part is supplied with the solution c by the capillary phenomenon of the filter paper 7c and is in a wetted state.

Furthermore, on the cathode side of the filter-paper bridge 7c of the chamber C, a movable mechanism 8 comprising a support leg 8a and a drawbridge plate 8b rotatably mounted on this support leg 8a is provided, and, on the surface on the anode side of the drawbridge plate 8b (the surface to contact the supporting medium 3 and the filter paper 7c at the time of use of the apparatus) is fixed a supporting medium for concentration (Separax-EF of 140 $\mu$m thickness cut to a size of 60×150 mm.) impregnated with a buffer solution (solution B) prepared by dissolving 7.51 g. of Tris in distilled water, adjusting the pH to 6.7 (in general, lower by 0.1 pH unit or more than those of the solution A and the solution C) with approximately 60 ml. of 1-normal hydrochloric acid, and then again adding distilled water to bring the volume to 1 liter.

One example of the general outline of operation in analyzing a sample solution by means of the apparatus of the above described construction will now be described.

First, cooling water (tap water) is circulated through the cooling water circulation chamber 4. Then the supporting medium 3 for separation and the supporting medium 9 for construction are immersed for 10 minutes or longer respectively in the solution A and the solution B, and the supporting media are wetted until equilibrium is attained. The filter paper 7a and the filter paper 7c are respectively immersed in the solution A and the solution C, and the filter paper 7c is placed on and over the support plate 6c to form the filter paper bridge 7c. 22 ml. of the solution A and 35 ml. of the solution C are respectively placed in the anode chamber and the cathode chamber. Next, the supporting medium 3 for separation is caused to adhere tightly to one surface of the glass plate (70×90×1 mm.), and, after surplus water has been absorbed with filter paper, the two members are placed with the surface of the supporting medium 3 on top on the platform forming the upper surface of the cooling water circulation chamber 4. At this time, the extreme end on the cathode side of the supporting medium 3 is brought into coincident alignment with the extreme end on the cathode side of the platform constituted by the cooling water circulation chamber 4. One end of the previously prepared filter paper 7a impregnated with the solution A is immersed in the solution A in the anode chamber A, while the other end is laid overlappingly with a superposition of, for example, approximately 5 mm. on the end of the anode side of the supporting medium 3 for separation. Next, the previously prepared supporting medium 9 for concentration impregnated with the solution B is caused to adhere tightly to the drawbridge plate 8b, and surplus water is absorbed with filter paper.

Thus, the organization of the apparatus illustrated in FIG. 1 is completed. Next, an example of the operation of separating protein in blood serum by using this apparatus will be described.

Figure 2:
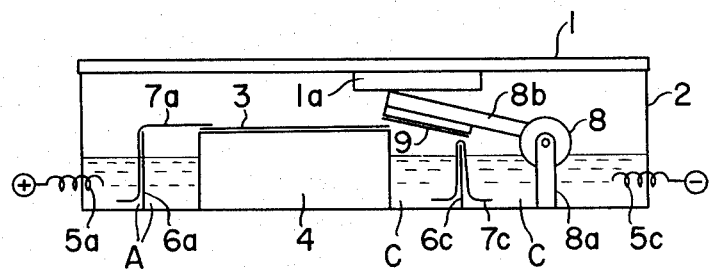
FIG. 2 is an arrangement view as viewed from the side of the operational state of the same apparatus.

Approximately 0.5 μl of blood serum is applied in the form of a straight line perpendicular to the straight line joining the electrodes 5a and 5c on substantially the middle part of the supporting medium 9 for concentration mounted on the drawbridge plate 8b by means, for example, of a micropipette. The application in this instance is not required to be as accurate as in a conventional method. The drawbridge plate 8b is then swung down, and the cover 1 is closed. A constant dc voltage of 200 V is impressed on the electrodes 5a and 5c, and the drawbridge plate 8b is pushed by a drawbridge plate holding device 1a (which can be any device such as an elastic member or a spring member) secured to the inner surface of the cover 1 thereby to secure contact between the supporting medium 9 for concentration and the supporting medium 3 for separation and the filter paper bridge 7c and to start the flow of electric current (of approximately 2 mA). The overlap of the supporting medium 9 and the supporting medium 3 and the contact width of the supporting medium 9 and the filter-paper bridge 7a are of the order of approximately 2 mm. This state is shown in FIG. 2.

By the above described operation, the proteins within the blood serum, while migrating to the anode side on the supporting medium 9 for concentration, are concentrated by being confined between the interfaces formed by the leading ions ($Cl^-$) contained in the solution A and the terminating ions (glycine$^-$ ions) contained in the solution C and, after assuming the form of a thin line, migrate onto the supporting medium 3 for separation, where, as they advance further toward the anode side, they are gradually separated into their various components.

By taking the supporting medium 3 for separation off the cooling chamber 4 after passing the electric current for approximately one hour, staining the separation pattern of the proteins, for example, with Ponceau S and measuring the concentrations in the pattern by means of a densitometer, the respective protein fractions can be quantitatively determined.

Experimental Example

By the process set forth in the above described example, separation of the proteins in the following three samples was carried out.

Sample 1: human blood serum, 0.5 μl applied.
Sample 2: human blood serum diluted 20 times, 10 μl applied.
Sample 3: human liver extract 25% (W/V), 10 μl applied.

Figure 3:
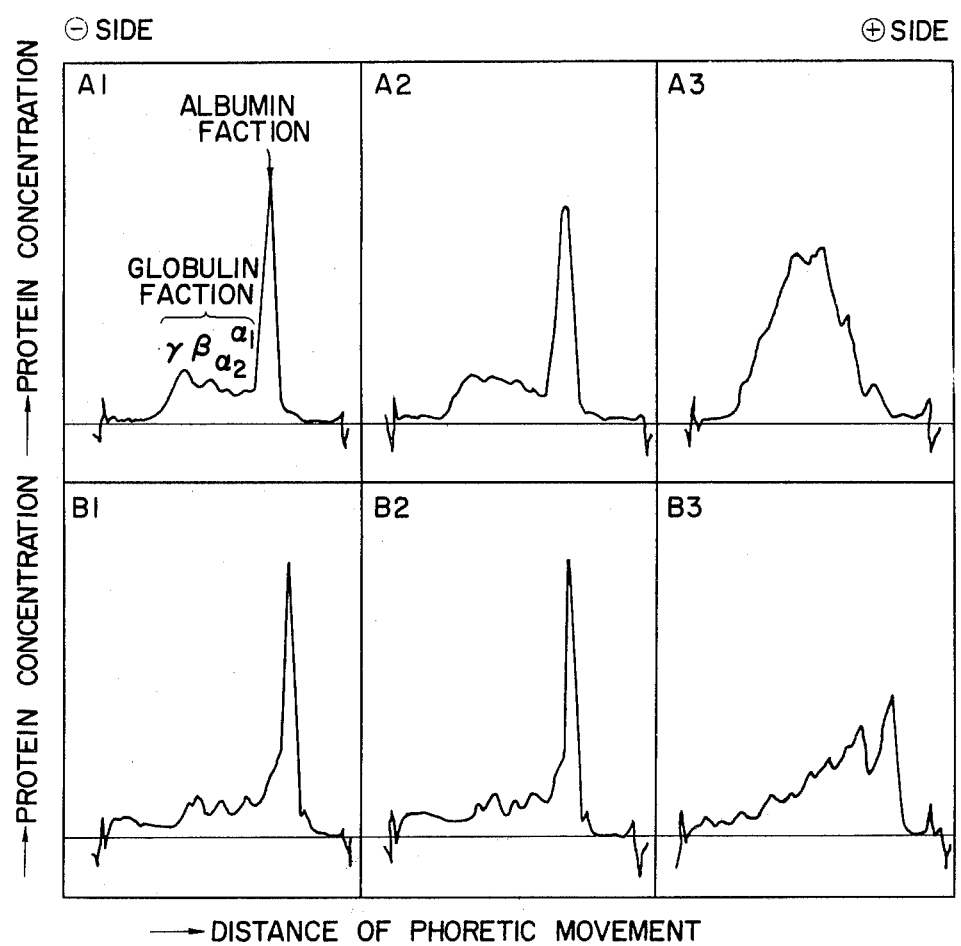
FIG. 3 comprises protein separation patterns in samples of three kinds each which were obtained through the process using the apparatus of this invention and a conventional process, A1 through A3 being those obtained through the conventional process and B1 through B3 being those obtained through the process of this invention.

After these samples were separated, the supporting medium 3 for separation (Separax-EF) was stained with Ponceau S, and the separation patterns of the proteins were measured with a densitometer (TLC scanner-CS-type 10, manufactured by Shimazu Seisaku-sho) and are shown as graphs of approximately ¼ reduced scale in B1 through B3 of FIG. 3.

The results of carrying out electrophoretic separation of the above described Samples 1 through 3 for the purpose of comparison by a conventional process, more specifically, by superposing a filter-paper bridge similar to that designated at 7a in FIG. 1 on both sides of the supporting medium 3 for separation (Separax-EF) of the above mentioned FIG. 1 or FIG. 2, placing a Tris/Veronal (that is, diethylbarbituric acid)/Veronal sodium (that is, sodium diethylbarbiturate) buffer solution (pH 8.8), and similarly passing electric current at 200 V for one hour, are shown in FIG. 3 A1 through A3.

When the separation patterns of FIG. 3 B1 through B3 are compared with those of FIG. 3 A1 through A3, the following observations can be made.

Thus, by the conventional process, in the case where blood serum of a small quantity (0.5 μl) such as Sample 1 is applied, a relatively good distribution pattern as indicated in FIG. 3 A1 is obtained, but when a diluted blood serum such as Sample 2 is applied in a great quantity (10 μl) so that the total proteins will be of the same quantity, the separation becomes very poor as indicated in FIG. 3 A2. In contrast, in the case of the process of this invention, a separation which is almost unchanged from that of Sample 1 (FIG. 3 B1) is obtained also in the case of Sample 2 (FIG. 3 B2). Furthermore, in the case of an extracted liquid from a living-body tissue such as liver, the application of a great quantity is required since the protein concentration is low from the beginning, but in such a case the separation by the conventional process is extremely poor (FIG. 3 A3), whereas, in contrast, in the case of the process of this invention, a very good separation pattern (FIG. 3 B3) is obtained.

Examples of Modifications

In the foregoing, this invention was described with respect to a specific example of practice. However, that various modifications can be made within the scope of this invention will be readily apparent to those skilled in the art. Some examples of such modifications are set forth below.

First, while chlorine ions were used as leading ions for carrying out electrophoresis with an alkaline pH (solution A) in the above described example, these may be phosphoric acid ions, and further, while glycine was used as terminating ions, ions of a weak acid or an amino acid having a pKa which is higher by 1 pH unit or less than the pH of the solution A are generally used.

Furthermore, an acidic buffer solution can also be used for the solution A. In this case, since the sample components to be separated are ordinarily charged positively, the electrode 5a is made the cathode and the electrode 5c the anode, and for the leading ions, for example, potassium, sodium, Tris (combined with phosphoric acid ions to impart a buffer characteristic in this case) and the like ions are used, while ions of a weak base or an amino acid having a pKa which is lower by 1 pH unit or less than the pH of the solution A are used for the terminating ions, the pH of the solution B, in general, being made higher by 0.1 pH unit or more than the pH of the solution A and the solution C.

In addition, with respect to the selection of the leading ions and the terminating ions or the selection of the buffer solutions, the practice known with regard to the disk electrophoresis method, basically, is applicable as it is.

Furthermore, the member 7c for supplying the solution C need not be a bridge as illustrated in the drawing but may be any member which can be wetted with the solution C such as, for example, the discharge port of a micropump, and, furthermore, without providing this separately, it can also be made in a form wherein, by changing the disposition of the drawbridge plate 8b, it is immersed in the solution C in the chamber C at the end opposite to the one end contacting the supporting medium for separation of the supporting medium 9 for concentration.

Furthermore, the material of the bridges 7a and 7c can be any water-retentive material other than filter paper such as cloth, unwoven fabric, fiber bundle or zeolite or some other porous solid. Moreover, the supporting medium 3 for separation and the supporting medium for concentration can be of any water-retentive membrane or sheet material other than cellulose acetate membrane such as, for example, any porous resin membrane, filter paper, cloth, unwoven fabric, fiber bundle, and other porous solid sheet, etc.

In addition, the drawbridge plate 8b need not be a rotating plate but may be one of up-and-down movement, and, for establishing contact between the supporting medium 9 for concentration and the supporting medium 3 for separation and the member 7 for supplying the solution C, instead of moving only the supporting medium 9 for concentration as shown in the drawing, at least one of the supporting medium 3 for separation and the member for supplying the solution C can be readily caused, depending on the necessity, to move together with the supporting medium 9 for concentration or in place thereof.

That is, the unique characteristic of this invention lies in the electrophoresis apparatus per se, which affords good effectiveness in concentrating and separating samples by causing the supporting medium 9 for concentration to contact the supporting medium 3 for concentration and the member 7c for supplying the solution C to contact mechanically prior to or substantially simultaneously with the electrophoresis rather than in the individual mechanical constructions for causing the contact between these members.

INDUSTRIAL APPLICABILITY

As described above, by the use of the concentrating electrophoresis apparatus of this invention, a membrane concentrating electrophoresis process which affords a concentration and separation effect comparable to that of the disk electrophoresis while retaining the advantages of simplicity and convenience possessed by the membrane electrophoresis becomes possible. Accordingly, concentration and separation of living-body components having biological activity and other charged particles can be readily carried out with high accuracy. Therefore, this invention is widely utilizable in fields wherein membrane electrophoresis apparatuses or disk electrophoresis apparatuses were heretofore used and can be utilized particularly in the medical supplies industry, the zymological industries, foodstuff manufacturing industries, etc., which handle biological substances.

The concentrating electrophoresis apparatus of this invention includes for an initial stage of its operation an electrophoretic concentrating apparatus as mentioned hereinbefore. This electrophoretic concentrating apparatus has an independent significance, being apart from phoretic separation. That is, as is apparent from the aforedescribed example of practice, prior to the occurrence of phoretic separation, concentration of the sample components occurs on the supporting medium 9 for concentration, whereby it is possible, for example, to cut off the concentrated portions together with the supporting medium thereby to take out concentrated samples. Such concentrated samples are in general, useful for analysis methods wherein a concentrated state is desirable.

We claim:

1. A concentrating electrophoresis apparatus comprising: supply means for a buffer solution containing terminating ions and electrically connected to one electrode of a direct-current or alternating-current superposed direct-current electric power source; a supporting medium for separation electrically connected to the other electrode of the power source and comprising a water-retentive membrane or sheet material wetted with a buffer solution containing leading ions; a supporting medium for concentration comprising a water-retentive membrane material wetted with a buffer solution containing leading ions and having a pH different from that of the buffer solution wetting the supporting medium for separation; and a movable mechanism for causing the supporting medium for concentration at its one end to contact the supply means and at its other end to contact the supporting medium for separation and imparting electrical connection through these supply means, supporting medium for concentration, and supporting medium for separation.

2. An apparatus according to claim 1 in which the supporting medium for separation and the supporting medium for concentration comprise cellulose acetate membranes.

3. An apparatus according to claim 1 in which the supply means for the buffer solution containing terminating ions is a bridge of filter paper immersed at at least one end thereof in the buffer solution and electrically connected via said buffer solution to said one electrode of the power source submerged therein.

4. An apparatus according to claim 1 in which the movable mechanism comprises a rotatable plate mechanism which comprises a combination of a support leg and a rotatable plate rotatably connected at its one end to the support leg, the supporting medium for concentration being mounted on one surface of the rotatable plate, and which is so adapted that, when the rotatable plate is rotated into an operational position, the supporting medium for concentration is caused to contact the supporting medium for separation and the supply means for the buffer solution containing terminating ions.

5. An apparatus according to claim 1 in which the movable mechanism is a vertically moving plate mechanism which comprises a vertically moving plate and a driving means thereof, and which is so adapted that, when the plate, on one surface of which the supporting medium for concentration is mounted, is moved vertically into an operational position, the supporting medium for concentration is caused to contact the supporting medium for separation and the supply means of the buffer solution containing terminating ions.

6. An apparatus according to claim 1 in which the supporting medium for separation is physically connected via a filter paper wetted with the buffer solution containing leading ions in which said other electrode of the direct-current power source is submerged to said buffer solution, whereby the supporting medium for separation is electrically connected to said other electrode.

7. An apparatus according to claim 1 in which the buffer solutions are alkaline, and the supporting medium for separation is connected to the anode, while the supply means for the buffer solution containing terminating ions is connected to the cathode.

8. An apparatus according to claim 7 in which the leading ions are selected from chlorine ions and phosphoric acid ions, and the terminating ions are selected from ions of weak acids and amino acids each having a pKa which is higher by 1 pH unit or less than the pH of the buffer solution containing leading ions, the buffer solution wetting the supporting medium for concentration having a pH which is lower by 0.1 or more than that of the buffer solution wetting the supporting medium for separation.

9. An apparatus according to claim 1 in which the buffer solutions are acidic, and the supporting medium for separation is connected to the cathode, while the supply means for the buffer solution containing terminating ions is connected to the anode.

10. An apparatus according to claim 9 in which the leading ions are selected from ions of potassium, sodium, and Tris, and the terminating ions are selected from ions of weak bases and amino acids each having a pKa which is lower by 1 pH unit or less than the pH of the buffer solution containing leading ions, the buffer solution wetting the supporting medium for concentration having a pH which is higher by 0.1 or more than that of the buffer solution wetting the supporting medium for separation.

11. An apparatus according to claim 9 in which: the entire apparatus is disposed within a vessel of relatively wide transverse dimension; a cooling water circulation chamber is disposed across the width of the vessel at substantially the middle thereof, whereby, on opposite sides of the cooling water circulation chamber within the vessel, a bath of the buffer solution for wetting the supporting medium for separation and a bath of the buffer solution containing terminating ions are respectively defined; and the supporting medium for separation is disposed on the upper surface of the cooling water circulation chamber.

* * * * *

UNITED STATES PATENT AND TRADEMARK OFFICE
CERTIFICATE OF CORRECTION

PATENT NO. : 4,297,198

DATED : October 27, 1981

INVENTOR(S) : Mochihiko Ohashi et al

It is certified that error appears in the above—identified patent and that said Letters Patent is hereby corrected as shown below:

On the title page, item (30), "53-64307" should read -- 53-64037 --.

*Signed and Sealed this*

*Thirteenth* Day of *April 1982*

[SEAL]

Attest:

Attesting Officer

GERALD J. MOSSINGHOFF

Commissioner of Patents and Trademarks